US008110396B2

(12) United States Patent
Bommer et al.

(10) Patent No.: US 8,110,396 B2
(45) Date of Patent: Feb. 7, 2012

(54) THERMOCYCLING DEVICE WITH A THERMAL SWITCH COMPRISING A MAGNETIC OR METAL THERMOCONDUCTING LIQUID AND A STIMULATING UNIT

(75) Inventors: Daniel Bommer, Winterhur (CH); Thomas Schlaubitz, Meggen (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 163 days.

(21) Appl. No.: 12/467,906

(22) Filed: May 18, 2009

(65) Prior Publication Data

US 2009/0291487 A1 Nov. 26, 2009

(30) Foreign Application Priority Data

May 20, 2008 (EP) .................................... 08009215

(51) Int. Cl.

| | |
|---|---|
| ***C12M 1/00*** | (2006.01) |
| ***C12M 3/00*** | (2006.01) |
| ***H01H 67/06*** | (2006.01) |
| ***H01F 7/08*** | (2006.01) |
| ***F02M 11/00*** | (2006.01) |

(52) U.S. Cl. ............... 435/303.1; 435/287.2; 435/288.4; 335/47; 335/220; 261/146; 261/151

(58) Field of Classification Search ............... 435/303.1, 435/287.2, 288.4; 335/47, 220; 261/146–151
See application file for complete search history.

(56) References Cited

U.S. PATENT DOCUMENTS

| | | | | |
|---|---|---|---|---|
| 6,533,255 | B1 | 3/2003 | Mitsuhashi et al. | |
| 2002/0166764 | A1 * | 11/2002 | MacPhee ................. | 204/403.14 |
| 2008/0003649 | A1 | 1/2008 | Maltezos et al. | |

FOREIGN PATENT DOCUMENTS

| | | | |
|---|---|---|---|
| EP | 08009215 | | 11/2008 |
| WO | 2004105947 | A2 | 12/2004 |
| WO | 2004105947 | A3 | 12/2004 |

* cited by examiner

*Primary Examiner* — Nathan Bowers
*Assistant Examiner* — Gautam Prakash
(74) *Attorney, Agent, or Firm* — M. Reza Savari

(57) ABSTRACT

The invention relates to a thermocycler module for heating and/or cooling of a thermocycling device comprising a thermal switch, a heating block and a heat sink. The thermal switch comprises a thermoconducting liquid, e.g. a magnetic fluid or a liquid metal, and a stimulating unit, e.g. a magnetic unit or a Lorentz-force unit, for moving the thermoconducting liquid. The movement of the thermoconducting liquid provides, in an on-state of the thermal switch, a thermal connection between the heating block and the heat sink.

15 Claims, 4 Drawing Sheets

THERMOCYCLING DEVICE WITH A THERMAL SWITCH COMPRISING A MAGNETIC OR METAL THERMOCONDUCTING LIQUID AND A STIMULATING UNIT

CROSS-REFERENCE TO RELATED APPLICATION

The present application claims the benefit of EP Appl. No. 08009215.8 filed May 20, 2008, the content of which is hereby incorporated herein by reference in its entirety.

FIELD OF THE INVENTION

The present invention relates to a thermocycling device comprising a thermocycler module, to a method of cooling a heating block in a thermocycler module with a heatsink of a thermocycling device and to an analytical apparatus.

DESCRIPTION OF PRIOR ART

Thermocycling devices comprising thermocycler modules are mainly used for an automatic procedure of polymerase chain reactions (PCR). During a conduct of a PCR the liquid PCR-samples have to be heated and cooled to several temperatures. Typically, at least two temperatures, preferably an annealing, an incubation and a denaturation temperature, have to be accessed and maintained in repetitive cycles. For denaturation, the heating block of the thermocycling device has to be heated to temperatures up to 105° C. Thus, the time for heating and cooling the sample has a great influence on the overall process time. A decrease in heating and cooling time is essential for an efficient and cost effective process and an increase in throughput of a thermocycling device.

So far, mainly thermoelectric modules (TEC) are used for a fast thermocycling device for cooling and heating of a sample block, which carries the samples. A rapid thermocycler is e.g. disclosed in U.S. Pat. No. 6,556,940. This thermocycler comprises a low thermal mass sample block, whose temperature can be modulated by a single TEC. The TEC functions as the heater and cooler of the sample block. On the opposite side of the TEC a heat sink is arranged, which is used as a thermal reservoir. The heat sink is either cooled or heated depending on whether the sample block is heated or cooled, respectively. To enhance thermal connection between the TEC and the sample block and the heat sink, usually a thermal grease or thermal interface material in sheet form (e.g. graphite foil) is applied at the connecting surfaces.

Drawbacks of this technology are the need of permanent power for the thermoelectric module, because otherwise, the thermoelectric module is a thermal bridge, which will equalize the temperature on both sides of the module. Furthermore, the permanent change in temperature and the associated thermal expansion and contraction leads to a migration of the thermoelectric module and the thermal interface sheet material and bad thermal contacts between the surfaces of the thermoelectric module and the surface of the device to be temperature controlled. Furthermore, thermoelectric modules are expensive and susceptible to interference.

SUMMARY OF THE INVENTION

In first aspect the invention relates to a thermocycling device comprising a thermocycler module for heating and/or cooling, said thermocycler module comprising a thermal switch, a heating block, and a heat sink, wherein the thermal switch comprises a thermoconducting liquid and a stimulating unit for moving the thermoconducting liquid to provide in an on-state of the thermal switch, a thermal connection between the heating block and the heat sink and, in an off-state of the thermal switch, a thermal disconnection between the heating block and the heat sink.

In a second aspect the invention relates to a method of cooling a heating block in a thermocycler module with a heat sink of a thermocycling device, wherein the heating block is thermally connected to the heat sink said method comprising the step of switching on a thermal switch, and moving a thermoconducting liquid of the thermal switch with a stimulating unit to provide a thermal connection between the heating block and the heat sink.

In a third aspect the invention relates to an analytical apparatus comprising a thermocycling device according to the invention.

DETAILED DESCRIPTION OF THE INVENTION

Figure 1:
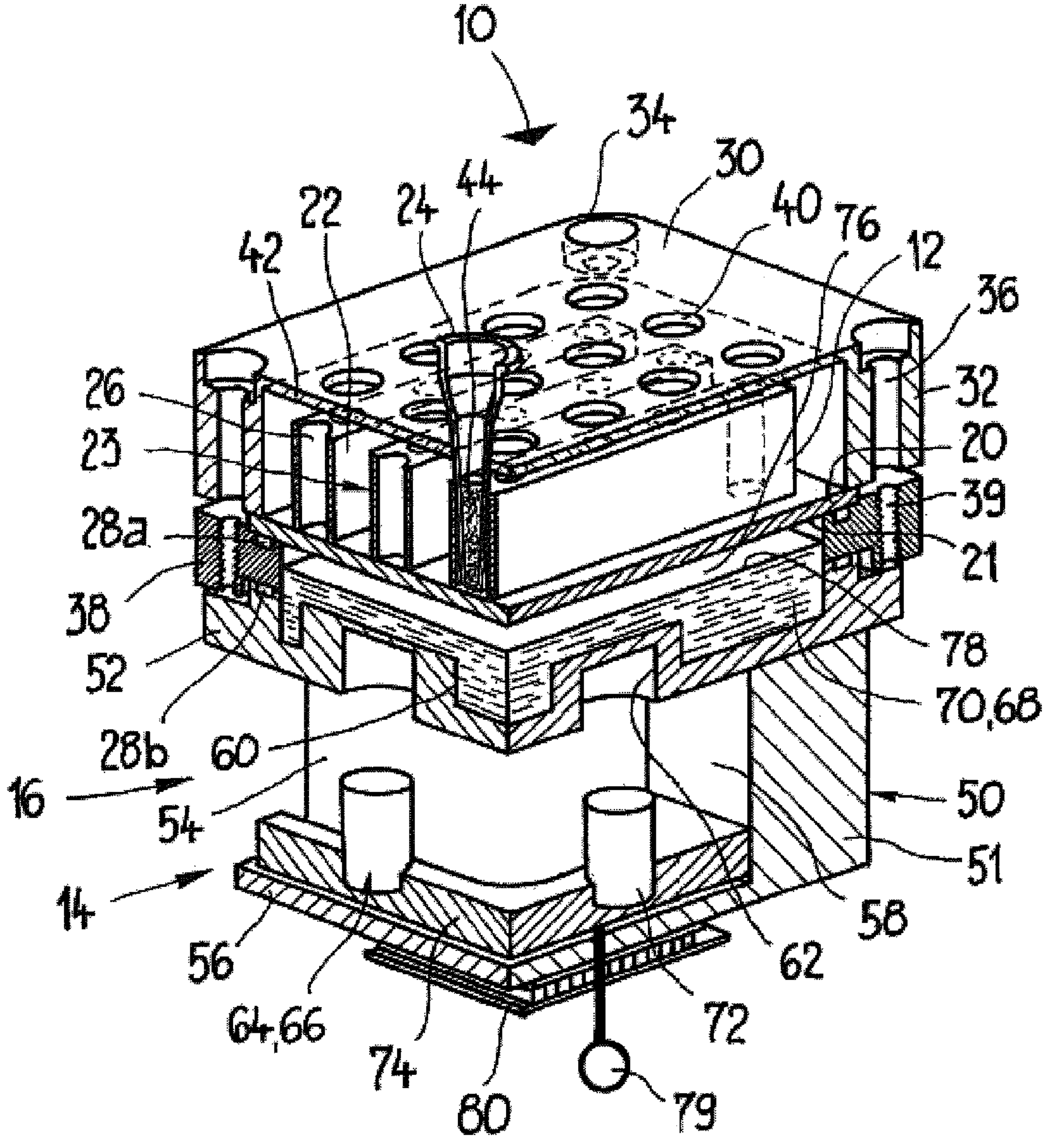
FIG. 1 shows a perspective cross-sectional schematic view of a first embodiment of a thermocycler module for heating and/or cooling with a magnet in a rest position and a thermal switch in the off-state.

It is an object of the present invention to provide a thermocycling device comprising a thermocycler module allowing quick, e.g. within seconds, heating and cooling steps in a reliable and highly reproducible manner.

Further objects of the present invention are to provide a method to cool a heating block in a thermocycler module of a thermocycling device by using a thermal switch and to provide an analytical apparatus.

The inventive thermocycling device comprises a thermocycler module for heating and/or cooling. The thermocycler module comprises a thermal switch, a heating block and a heat sink. The thermal switch comprises a thermoconducting liquid and a stimulating unit for moving the thermoconducting liquid. In an on-state of the thermal switch, a thermal connection between the heating block and the heat sink is provided by the thermoconducting liquid and, in an off-state of the thermal switch, the thermal connection is disconnected.

The thermocycling device according to the invention has the advantage that only a small thermal load is to be heated. On the other hand, a heat sink is reliably connected and disconnected to the heating block with low thermal boundary resistance and high thermal conductivity. This allows a fast and reliable modulation of a temperature of the heating block without susceptible and expensive parts. Further, no detection of the position of the thermoconducting liquid is required since the thermoconducting liquid moves down under gravity when the stimulating unit is switched off.

Heating blocks used in thermocycling devices are heat conductive blocks comprising at least one cavity for receiving a reaction receptacle. Commonly the material of these heating blocks comprises aluminum or silver. In the thermocycling device, the heating block is controlled to change between at least two temperatures, for example an annealing, an incubation and an denaturation temperature, in one cycle. The temperature of the heating block can be changed very quickly by means of the thermal switch, which controls the transfer of heat between the heating block and the thermal sink. The thermal switch controls the thermal connection and disconnection of the heating block and the heat sink.

In a certain embodiment of the thermocycling device according to the present invention, the thermoconducting liquid -may comprise or may be a magnetic fluid and the stimulating unit may comprise a magnetic unit for moving the magnetic fluid in order to connect and/or disconnect the thermal connection between the heating block and the heat sink. Alternatively, the thermoconducting liquid may comprise or may be a liquid metal and the stimulating unit comprises a Lorentz-force unit for moving the liquid metal in order to connect and/or disconnect the thermal connection between the heating block and the heat sink. These embodiments have a simple design and work reliably.

A further aspect of the present invention is to switch the thermal switch by deforming a surface of the magnetic fluid by the magnetic unit or of the liquid metal by the Lorentz-force unit.

Another aspect of the present invention is to arrange the magnetic fluid and the liquid metal, respectively, at least partially between the heat sink and the heating block. In an off-state of the thermal switch, a gap is present between the magnetic fluid and the liquid metal, respectively, and the heating block. Thus, the heating block is thermally isolated with respect to the magnetic fluid and the heat sink.

The method for cooling a heating block in a thermocycler module of a thermocycling device according to the invention is based upon switching on a thermal switch, which in an on-state provides a connection between a heating block and a heat sink via a thermoconducting liquid, particularly a magnetic fluid or a liquid metal.

An analytical apparatus according to the present invention has the same advantages as the thermocycling device.

Further preferred embodiments are endowed with features contained in further depending claims.

FIG. 1 shows a thermocycler module 10 with a heating block 12 above a heat sink 14 and a thermal switch 16 in-between. The heating block 12 comprises a base-plate 20 and vial-walls 22 fixed at or integrally formed with the base-plate 20. A number of reaction vials 24 (only one is shown) are loaded from above in loading recesses formed as blind holes 26. Due to this configuration, the thermal mass of the heating block 12 is relatively low compared with the heat sink's 14 thermal mass. The heating block 12 can be heated by an incorporated, well known heater element 23, e.g. a heated fluid or an electrical heater, indicated by an arrow.

A cover 30 of the heating block 12 has a thick circumferential border wall 32. At corners 34 of the circumferential border wall 32 there are fixation throughput holes 36. The fixation throughput holes 36 serve to accommodate fixation screws.

A frame 38 surrounds the upper border of the heat sink 14 and is fixed to the heat sink 14, e.g. with further screws. In the corners of the frame 38 there are holes 39 with inner threads arranged as a prolongation of the fixation throughput holes 36, so that the fixation screws can be screwed in these holes 39 to fix the cover 30 to the frame 38. An upper inner border part of the frame 38 supports the bottom border part of the base-plate 20.

By fixation of the cover 30, the base surface of the circumferential border 32 partially presses against the upper circumferential border of the base plate 20 of the heating block 12. The circumferential border of the base plate 20 is otherwise supported by the frame 38. Thus, the heating block 12 is fixed via the frame 38 to the heat sink 14. Additional circumferential grooves 28*a*, 28*b* arranged at upper border parts of the frame 38 and the heat sink 14, respectively, accommodate an o-seal to seal a space enclosed by the heating block 12, heat sink 14 and frame 38.

The cover 30 and the frame 38 may be made at their connecting parts of a material with low or no thermal conductivity or the cover 30 and the frame 38 are thermally isolated against the other parts in touch with them. Thus the frame 38 thermally isolates the heating block 12 against the heat sink 14. This also provides a relative low thermal mass of the heating block 12 and allows a rapid temperature modulation of the heating block i.e. the reagent.

The cover 30 comprises in its upper plate 42 vial-throughput-holes 40 above each blind hole 26 of the vial-walls 22 to allow the reaction vials 24 to be placed in the blind holes 26. The reaction vials 24 are filled with a reagent 44.

The heat sink 14 comprises a body 50 and a cap 52. The body 50 is formed of a wall-section 51, a column-section 54 and a bottom-section 56. The cap 52 and the body 50 enclose a ring-shaped clearance 58 around the column-section 54. The upper surface of the cap 52 forms a trough 60 which is open towards a bottom side 21 of the base plate 20. The lower surface of the cap 52 comprises four accommodation recesses 62, formed as bind-holes with openings facing away from the heating block 12 into the clearance 58.

The thermal switch 16 comprises a stimulating unit 64 designed as a magnetic unit 66 and a thermoconducting liquid 68 in form of a magnetic fluid 70, e.g. a Ferrofluid (FerroTec APGxxx). The magnetic liquid 70 is carried in the trough 60 of the heat sink 14. The magnetic unit 66 comprises four permanent magnets 72, e.g. in a cylindrical form, which are fixed with their bottom parts in openings of a frame-plate 74. The upper part of the permanent magnets 72 project out of the frame-plate 74 in the direction towards the cap 52. The frame-plate 74 encloses the column-section 54 and is placed in the clearance 58, so that the frame plate 74 with the permanent magnets 72 can be displaced vertically along the column-section 54 in the perpendicular direction to the bottom-section 56. The permanent magnets 72 are shown in the rest position in FIG. 1. Well known driving means 79 are connected to the frame-plate 74. The driving means 79 can also be placed in the wall-section 51 or in the column-section 54.

The magnetic fluid 70 is arranged between the heat sink 14 and the heating block 12. A space 76 defining a gap is present between the magnetic fluid 70 and the heating block 12 in the off-state of the thermal switch 16, when the permanent magnets 72 are in their rest-position away from the cap 52, shown in FIG. 1. In particular the gap is present between the upper surface 78 of the magnetic fluid 70 carried in the trough 60 and the bottom side 21. The upper surface 78 of the magnetic fluid 70 is opposite the bottom side 21.

The space 76 isolates thermally the heat sink 14 from the heating block 12. The connection via the frame 38 has a high thermal resistance. In the space 76 air or an other gas can be present. According to the present invention, It is also possible to improve the thermal isolation by evacuating the space 76 between the heating block 12 and the heat sink 14 enclosed by the frame 38. The vacuum may also fix the base plate 20 on the frame 38 and thus the heating block 12 on the heat sink 14.

A thermoelectric module 80 is arranged underneath the bottom-section 56 of the heat sink 14, to hold a temperature of the heat sink 14 on a constant value or a predetermined temperature profile.

Figure 2:
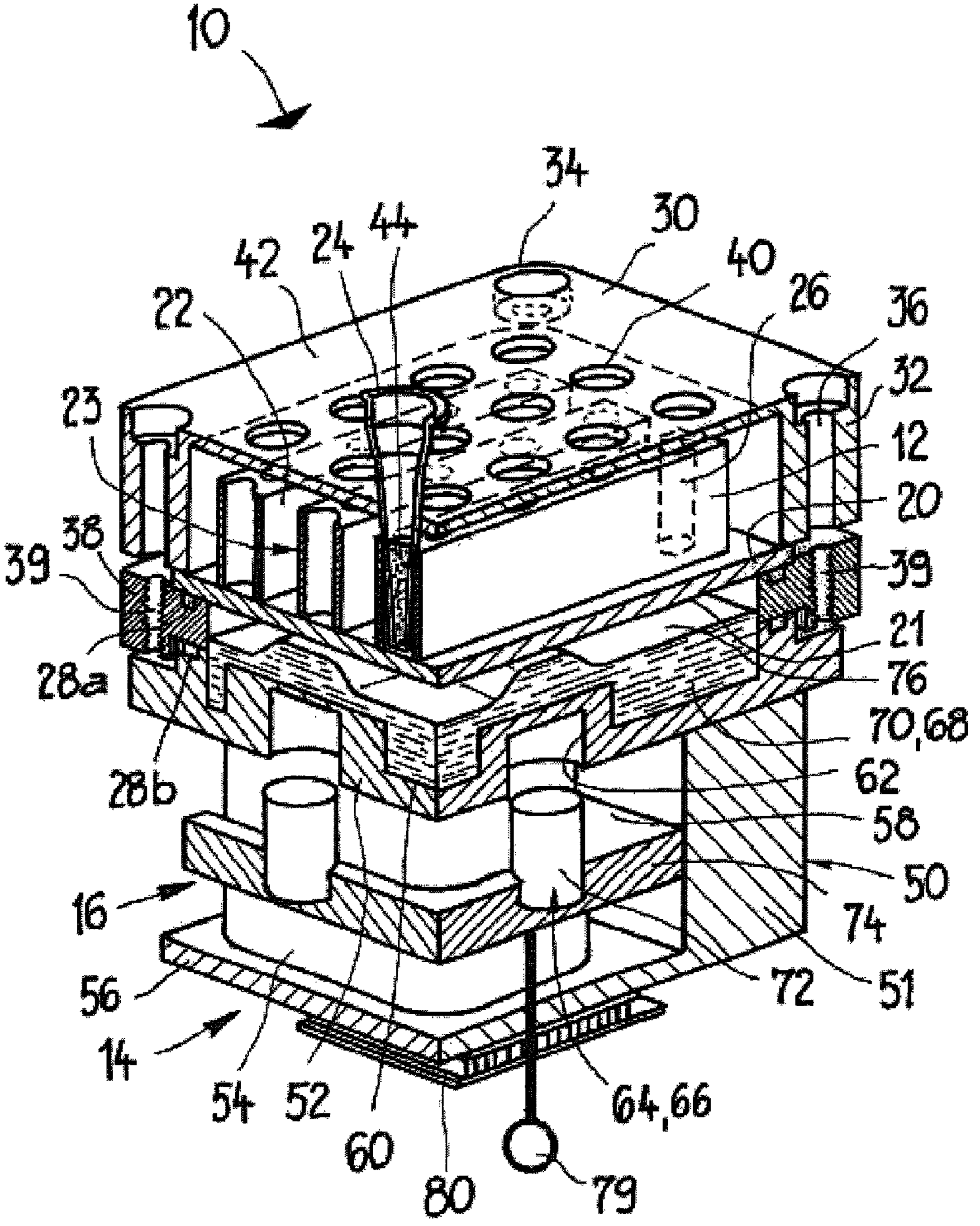
FIG. 2 shows a perspective cross-sectional schematic view of the thermocycler module shown in FIG. 1 with the magnet and the thermal switch in an intermediate state.

In an intermediate position shown in FIG. 2 the frame-plate 74 is moved by the driving means 79 towards the cap 52. Due to the increased interference of the magnetic field of the permanent magnets 72 and the magnetic liquid 70, little bumps are formed in the upper surface 78.

Figure 3:
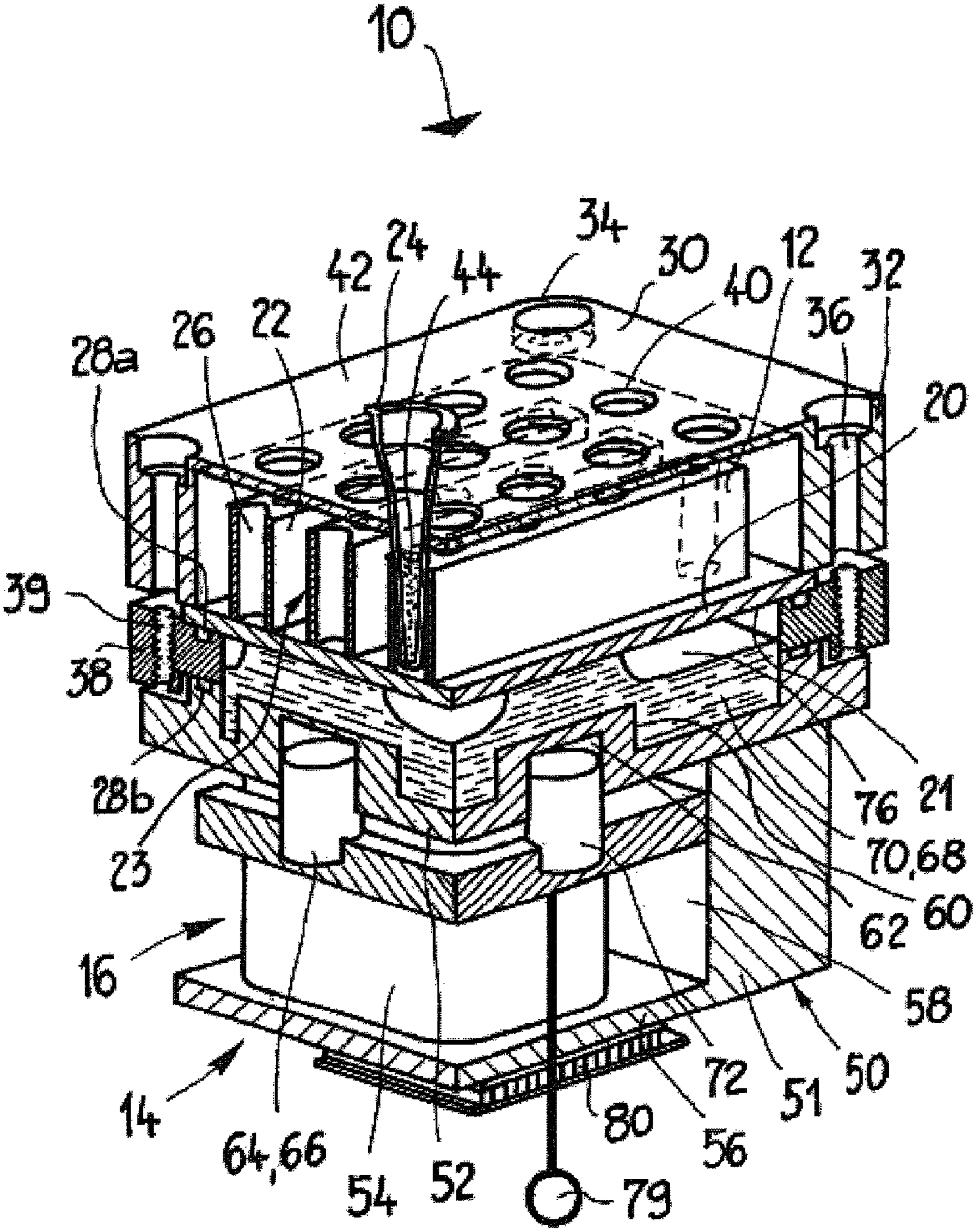
FIG. 3 shows a perspective cross-sectional schematic view of the thermocycler module shown in FIG. 1 and FIG. 2 with the magnet in an active position and the thermal switch in an on-state.

FIG. 3 shows the active position of the permanent magnets 72. The upper part of the permanent magnets 72 are at least partially accommodated by the accommodation recesses 62. In the corresponding on-state of the thermal switch 16, the magnetic field of the magnetic means, i.e. the permanent magnets 72, deform a surface of the magnetic fluid 70. The upper surface 78 is at least partially in contact with the bottom side 21 of the base plate 20 of the heating block 12. A bottom surface of the magnetic fluid 70 is always in contact with a surface of the trough 60. Thus a thermal connection is provided between the heating block 12 and the heat sink 14 to cool the heating block 12. This cooling is provided within seconds, because the thermal mass of the heat sink 14 is much higher than the thermal mass of the heating block 12. Therefore, it is beneficial to design the heating block 12 with a relative low mass as explained above.

FIG. 1, FIG. 2, and FIG. 3 show a course of action of the thermal switch 16 from an off-state (FIG. 1) to an intermediate state (FIG. 2) up to an on-state (FIG. 3) of the thermal switch 16.

By driving the frame-plate 74 with the driving means 79 and hence, the permanent magnet 72 from a rest position shown in FIG. 1 to an intermediate position shown in FIG. 2 up to an active position shown in FIG. 3 a magnetic field of the permanent magnet 72 interferes more and more with the magnetic liquid 70. The result is, that the upper surface 78 of the magnetic liquid 70 begins to deform and the surface is partially moved against the base plate 20 of the heating block 12 until the upper surface 78 is at least partially in contact with the heating block 12. Hence, the thermal switch 16 is switched on. Due to the thermal switch's low thermal contact resistance, the high thermal conductivity of the magnetic liquid 70 and the heat sink's relative large thermal mass, the heating block 12 is cooled within seconds to the desired temperature.

To switch off the thermal switch 16 the driving means 79 have to move the frame-plate 74 from the active position (FIG. 3) to the rest position (FIG. 1), so that the magnetic field of the permanent magnets 72 have a negligible interference with the magnetic fluid 70. The heater element 23 is switched alternately with the thermal switch 16, so that the heater element 23 has to heat only the relative low thermal mass of the heating block 12. The heating block 12 is heated by the heater-element 23 to the desired temperature within seconds.

Figure 4:
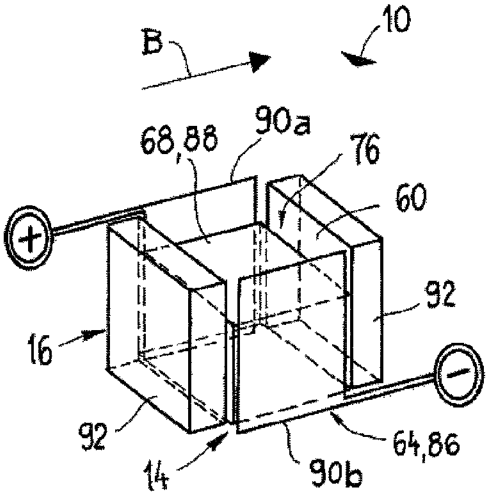
FIG. 4 shows a perspective cross-sectional schematic view of a thermal switch of a second embodiment of the thermocycler module for heating and/or cooling with a Lorentz-force unit, the thermal switch being in an off-state.
Figure 5:
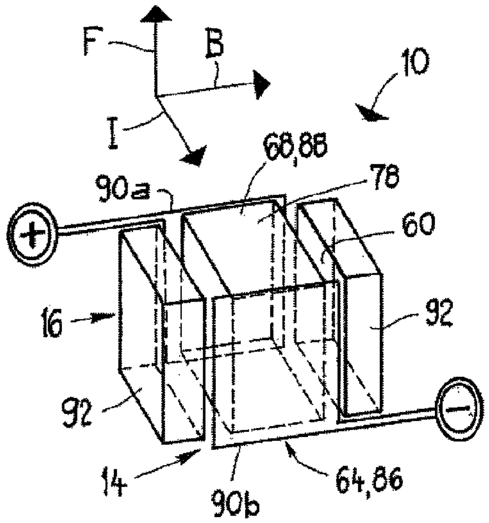
FIG. 5 shows the thermal switch in the on-state in the same view as FIG. 4.

FIGS. 4 and 5 show an alternative embodiment of the heat sink 14 with thermal switch 16 of the thermocycler module 10. The thermal switch 16 comprises a Lorentz-force unit 86 as stimulating unit 64 and a liquid metal 88, e.g. GaInS as thermoconducting liquid 68. The liquid metal 88 is carried in the trough 60 of the heat sink 14. The opening of the trough 60 in the form of a cuboid is laterally delimited by four side wall-sections and at the bottom side by a bottom wall-section of the heat sink 14. A thermoelectric module is arranged underneath the bottom wall-section to hold the temperature of the heat sink 14 on a constant value or a predetermined temperature profile; c.p. FIG. 1 to 3.

The heating block 12 as shown in FIG. 1 to 3 is arranged above the heat sink 14 so that the bottom side 21 of the base plate 20 of the heating block 12 delimits the opening of the trough 60 at the upper side. A thermal isolation is present between the heat sink 14 and the heating block 12.

Two opposing side wall-sections of the body of the heat sink 14 comprise each at the surface directed toward the opening of the trough 60 an electrode plate **90*a* and 90*b*, respectively. The electrode plate 90*a* of the one of the two side wall-sections is connected to a positive output connection (+) and the electrode plate 90*b*** of the other of these two side wall-sections is connected to a negative output connection (−) of an electrical control unit.

A permanent magnet 92 is assigned to each of the residual two opposing side wall sections. The permanent magnet 92 generates a magnetic field B in the opening of the trough 60.

As shown in FIG. 4, in the off-state of the thermal switch 16 no electrical tension is applied to the electrode plates **90*a*, 90*b* and no electrical current is flowing in the liquid metal 88 being in contact with the electrode plates 90*a*, 90*b*. A space 76 defining a thermal isolation gap is present between the liquid metal 88 and the bottom side 21 of the heating block 12**.

FIG. 5 shows the on-state of the thermal switch 16. The electrical control unit applies a voltage to the electrode plates **90*a* and 90*b*, thus an electrical current I is flowing through the liquid metal 88 from the electrode plate 90*a* to the electrode plate 90*b*. This electrical current I and the magnetic field B generate a force F deforming the liquid metal 88 and moving the upper surface 78 of the liquid metal 88 upwardly until the liquid metal 88 is in contact with the bottom side 21 of the heating block 12. Thus, the heating block 12 is cooled within seconds to the desired temperature. Thereby, the bottom surface of the liquid metal 88** remains in contact with the bottom wall-section of the trough.

Figure 6:
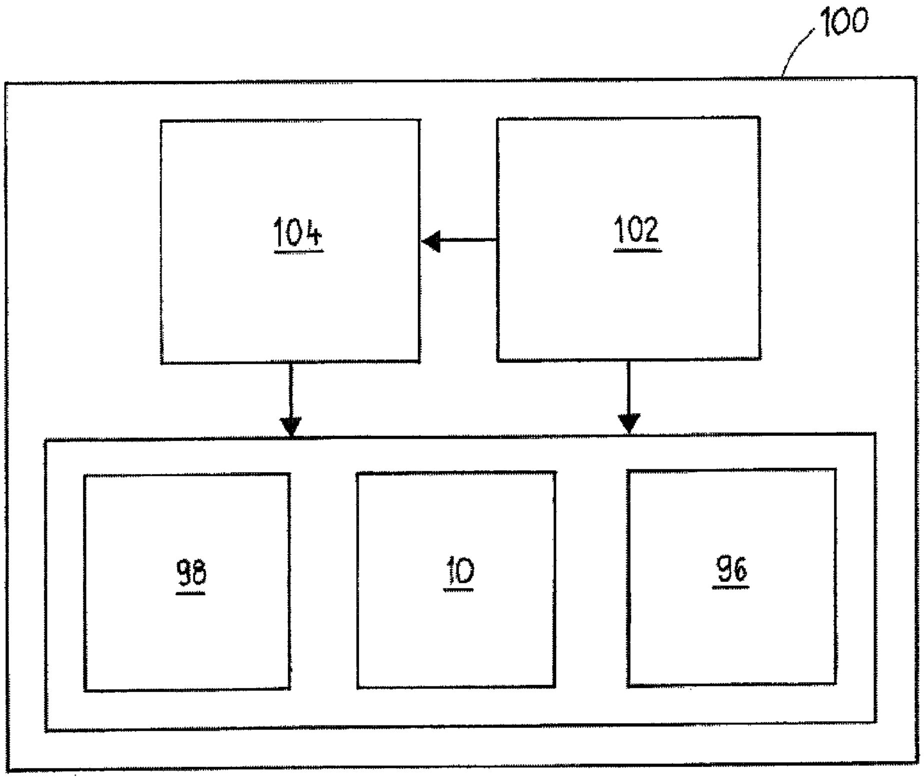
FIG. 6 shows a schematic representation of an analytical apparatus comprising a thermocycling device with a thermocycler module and further modules.

A thermocycling device according to the present invention and schematically shown in FIG. 6 comprises a thermocycler module 10, two embodiments of this thermocycler module 10 are shown in FIG. 1 to 5 and described above.

The thermocycling device may further comprise a defection unit 96, for example an optical defection unit for determining the amount of nucleic acid analyte produced during amplification in the thermocycler module 10. In a certain embodiment, the TaqMan methodology is used for simultaneous amplification and defection of the nucleic acid analyte by measuring the intensity of fluorescent light, as disclosed in WO 92/02638 and the corresponding documents U.S. Pat. No. 5,210,015, U.S. Pat. No. 5,804,375 and U.S. Pat. No. 5,487,972.

The thermocycling device may for example also comprise a heated lid 98 for covering the reaction receptacles (e.g. reaction vials 24) held by the heating block 12.

As further shown in FIG. 6, an analytical apparatus 100 comprises a thermocycling device according to the present invention. The analytical apparatus 100 may further comprise a storage module 102 for storing consumables used during the analytical test. Furthermore, a sample preparation module 104 may be comprised in the analytical apparatus 100. In the sample preparation module 104, a sample comprising analyte which was obtained from a biological sample is prepared such that the analyte, preferably a nucleic acid analyte, can be analysed by amplification. In a certain embodiment all steps carried out in the analytical apparatus 100 are fully automated.

The use of a thermoconducting liquid 68 has several advantages. The thermal connection can be connected and disconnected with a high reliability. Since the thermoconducting liquid 68 coats the base plate very efficiently, the surface connection to the base plate 20 in the on-state of the thermal switch 16 provides a very low thermal boundary resistance. The thermoconducting liquid 68 itself, in the form of a magnetic fluid 70 or a liquid metal 88, has a high thermal conductivity compared to thermal greases. In the off-state, the thermoconducting liquid 68 disconnects promptly without any residues at the base plate 20. Furthermore, in comparison to thermal greases, no degradation due to evaporation of grease compounds and no air enclosures occur. In the off-state no material filaments remain between the heating block 12 and the heat sink 14.

In a further embodiment of the invention the permanent magnets 72 of the embodiment shown in FIG. 1 to 3 are replaced by electromagnets, e.g. an inductor. The inductors can be switched on and off by simple, well known electrical switching means and can be installed fixed under the magnetic liquid 70. Thus, this further embodiment of the thermocycler module 10 as well as the embodiment disclosed in FIGS. 4 and 5 do not require movable parts with the exception of the thermoconducting liquid 68. The permanent magnets 92 of the Lorentz-force unit 86 can also be replaced by electromagnets.

| Reference numerals | |
|---|---|
| 10 | thermocycler module |
| 12 | heating block |
| 14 | heat sink |
| 16 | thermal switch |
| 20 | base-plate |
| 21 | bottom side base plate 21 |
| 22 | vial-walls |
| 23 | heater element |
| 24 | reaction vials |
| 26 | blind holes |
| 28a | circumferential groove |
| 28b | circumferential groove |
| 30 | cover |
| 32 | circumferential border wall |
| 34 | corners of circumferential border wall 32 |
| 36 | throughput holes |
| 38 | frame |
| 39 | holes |
| 40 | vial-throughput-holes |
| 42 | upper plate |
| 44 | reagent |
| 50 | body of heat sink 14 |
| 51 | wall-section 51 of body 50 |
| 52 | cap |
| 54 | column-section of body 50 |
| 56 | bottom-section of body 50 |
| 58 | ring-shaped clearance |
| 60 | trough |
| 62 | recesses |
| 64 | stimulating unit |
| 66 | magnetic unit |
| 68 | thermoconducting liquid |
| 70 | magnetic fluid |
| 72 | permanent magnet |
| 74 | frame-plate |
| 76 | space |
| 78 | upper surface of the magnetic fluid |
| 79 | driving means |
| 80 | thermoelectric module |
| 86 | Lorentz-force unit |
| 88 | liquid metal |
| 90a | electrode plate |
| 90b | electrode plate |
| 92 | permanent magnet |
| 96 | defection unit |
| 98 | heated lid |
| 100 | apparatus |

-continued

| Reference numerals | |
|---|---|
| 102 | storage module |
| 104 | preparation module |

While the foregoing invention has been described in some detail for purposes of clarity and understanding, it will be clear to one skilled in the art from a reading of this disclosure that various changes in form and detail may be made without departing from the true scope of the invention. For example, the systems and methods described above may be used in various combinations. All publications cited in this application are incorporated by reference in their entirety for all purposes to the same extent as if each individual publications were individually indicated to be incorporated by reference for all purposes.

What is claimed is:

1. A thermocycling device comprising:

a thermocycler module for heating and/or cooling, said thermocycler module comprising:
- a heating block,
- a heat sink arranged underneath the heating block, and
- a thermal switch comprising:
  - a magnetic thermoconducting liquid arranged between the heat sink and the heating block, the magnetic thermoconducting liquid comprising an upper surface and a lower surface in thermal connection with the heat sink,
  - a space defining a gap between the upper surface of the magnetic thermoconducting liquid and the heating block thermally isolating the heat sink from the heating block in an off-state of the thermal switch, and
  - a magnetic stimulating unit configured to move the magnetic thermoconducting liquid through the gap toward the heating block in an on-state of the thermal switch and upon contact of the upper surface of the magnetic thermoconducting liquid with the heating block making a thermal connection between the heating block and the heat sink.

2. The thermocycling device as in claim 1, wherein, in the on-state, a magnetic field of the magnetic stimulating unit deforms a surface of the magnetic thermoconducting fluid to provide the thermal connection between the heating block and the heat sink.

3. The thermocycling device as in claim 2, wherein the magnetic thermoconducting fluid is arranged at least partially between the heat sink and the heating block.

4. The thermocycling device as in claim 3, wherein, the magnetic thermoconducting fluid is carried in a trough of the heat sink, the trough is open towards a bottom side of the heating block and an upper surface of the magnetic thermoconducting fluid is opposite the bottom side of the heating block.

5. The thermocycling device as in claim 4, wherein, in the on-state, the upper surface of the magnetic thermoconducting fluid is at least partially in contact with the bottom side of the heating block and a bottom surface of the magnetic thermoconducting fluid is in contact with a surface of the trough.

6. The thermocycling device as in claim 1, wherein the heat sink comprises an accommodation recess with an opening facing away from the heating block, the accommodation recess is capable to accommodate the magnetic stimulating unit.

7. The thermocycling device as in claim 1, wherein the magnetic stimulating unit comprises a permanent magnet, which is movably arranged underneath the magnetic thermoconducting fluid and configured for moving between a rest-position and an active-position; the active-position corresponding to the on-state of the thermal switch and the rest-position corresponding to the off-state of the thermal switch.

8. The thermocycling device as in claim 7, wherein the permanent magnet is accommodated at least partially in an accommodation recess of the heat sink in the active-position and placed out of the accommodation recess in the rest-position.

9. The thermocycling device as in claim 1, wherein the magnetic thermoconducting fluid is a ferromagnetic metal, which is liquid over the temperature range in use of the thermocycling device.

10. An analytical apparatus comprising the thermocycling device as in claim 1.

11. A thermocycling device comprising:

- a thermocycler module for heating and/or cooling, said thermocycler module comprising:
  - a heating block,
  - a heat sink arranged underneath the heating block, and
  - a thermal switch comprising:
    - a thermoconducting liquid metal arranged between the heat sink and the heating block, the thermoconducting liquid metal comprising an upper surface and a lower surface in thermal connection with the heat sink,
    - a space defining a gap between the upper surface of the thermoconducting liquid metal and the heating block thermally isolating the heat sink from the heating block in an off-state of the thermal switch, and
    - a Lorentz-force stimulating unit configured to move the thermoconducting liquid metal through the gap toward the heating block in an on-state of the thermal switch and upon contact of the upper surface of the thermoconducting liquid metal with the heating block making a thermal connection between the heating block and the heat sink.

12. The thermocycling device as in claim 11, wherein the thermoconducting liquid metal is arranged at least partially between the heat sink and the heating block.

13. The thermocycling device as in claim 12, wherein, the thermoconducting liquid metal is carried in a trough of the heat sink, the trough is open towards a bottom side of the heating block and an upper surface of the thermoconducting liquid metal is opposite the bottom side.

14. The thermocycling device as in claim 13, wherein, in the on-state, the upper surface of the thermoconducting liquid metal is at least partially in contact with the bottom side of the heating block and a bottom surface of the thermoconducting liquid metal is in contact with a surface of the trough.

15. An analytical apparatus comprising the thermocycling device as in claim 11.

* * * * *